(12) United States Patent
Fremont et al.

(10) Patent No.: US 7,527,938 B2
(45) Date of Patent: May 5, 2009

(54) METHODS FOR DIAGNOSIS AND TREATMENT OF CHRONIC IMMUNE DISEASES

(75) Inventors: Marc Fremont, Vccle (BE); Patrick Englebienne, Zingem (BE); C. V. Taylor Herst, Oakland, CA (US)

(73) Assignee: R.E.D. Laboratories N.V./S.A., Zellik (BE)

( * ) Notice: Subject to any disclaimer, the term of this patent is extended or adjusted under 35 U.S.C. 154(b) by 774 days.

(21) Appl. No.: 10/174,521

(22) Filed: Jun. 17, 2002

(65) Prior Publication Data

US 2003/0077674 A1    Apr. 24, 2003

Related U.S. Application Data

(60) Provisional application No. 60/299,323, filed on Jun. 19, 2001.

(51) Int. Cl.
*G01N 33/48* (2006.01)
*G01N 33/564* (2006.01)
*G01N 33/68* (2006.01)

(52) U.S. Cl. .................. 435/7.24; 435/7.21; 435/4; 436/506; 436/63; 436/811; 436/83; 530/300; 530/350

(58) Field of Classification Search .................. None
See application file for complete search history.

(56) References Cited

U.S. PATENT DOCUMENTS

| | | | |
|---|---|---|---|
| 5,766,859 A | 6/1998 | Vojdani et al. |
| 5,776,690 A | 7/1998 | Vojdani et al. |
| 5,830,668 A | 11/1998 | Mordechai et al. |
| 5,853,996 A | 12/1998 | Mordechai et al. |
| 5,985,565 A | 11/1999 | Suhadolnik |
| 6,153,591 A | 11/2000 | Cai et al. |
| 6,184,210 B1 | 2/2001 | Keana et al. |

FOREIGN PATENT DOCUMENTS

WO    WO 91/00097 A1    1/1991

OTHER PUBLICATIONS

Beers et al, The Merck manual, 17th edition, Merck Research Laboratories, 1999, pp. 1024-1026, 1041, 1061-1063.*
Komaroff et al., (2000), *Am. J. Med.*, 108:69-71.
King et al., (1998), *J. Biol. Chem.*, 273(15):8699-8704.
Wong et al., (1997), *The EMBO J.*, 16(6):1291-1304.
Bottrel et al., (1999), *Antimicrob. Agents Chermother.*, 43(4):856-861.
Yang et al., (2000), *Proc. Nat. Acad. Sci.*, 97(25):13631-13636.

* cited by examiner

*Primary Examiner*—Michael Pak
*Assistant Examiner*—Nirmal S Basi
(74) *Attorney, Agent, or Firm*—Bret E. Field; Bozicevic Field & Francis LLP.

(57) ABSTRACT

Methods are provided for diagnosing and/or characterizing chronic immune disease activity in a subject. In the subject methods, a sample is obtained from a subject suspected of having or known to have a chronic immune disease. The sample is then assayed for the presence of native Stat-1 protein and/or any lower molecular weight fragments of Stat-1 protein present. The assay results are used to diagnose the presence of chronic immune disease activity and/or characterize chronic immune disease activity in the subject, e.g., to confirm an initial chronic immune disease diagnosis, to determine the stage of the disease, to monitor disease progression, to predict disease attacks, and the like. In certain embodiments, the assay results are also used to predict the effectiveness of a particularly treatment protocol, e.g., to determine whether an interferon based treatment protocol will be effective. In addition, methods of Stat-1 based methods of treating chronic immune disease conditions are provided. Also provided by the subject invention are kits for practicing the methods.

6 Claims, 4 Drawing Sheets

METHODS FOR DIAGNOSIS AND TREATMENT OF CHRONIC IMMUNE DISEASES

CROSS REFERENCE TO RELATED APPLICATIONS

Pursuant to 35 U.S.C. § 119(e), this application claims priority to the filing date of the U.S. Provisional Patent Application Ser. No. 60/299,323 filed Jun. 19, 2001; the disclosure of which are herein incorporated by reference.

INTRODUCTION

1. Technical Field

The field of invention is chronic immune disease, particularly multiple sclerosis and chronic fatigue syndrome.

2. Background of the Invention

Chronic immune diseases can be highly debilitating, often requiring treatment. Two such chronic immune diseases are multiple sclerosis and chronic fatigue syndrome.

Multiple sclerosis (MS) is a neurological illness of unknown etiology associated with attacks of focal or multifocal neurological dysfunction indicating lesions within the central nervous system (CNS). In America and Northern Europe, MS is the most common neurological disease, with prevalence rates estimated between 50-100 per 100,000 population. The onset of disease is most common in early adulthood. Recurrent attacks can occur over many years, with approximately 30 percent of the patients progressing to a severe form of the disease which can be fatal.

MS is pleomorphic in its presentation. The clinical manifestations are determined in part by the location of the foci of demyelination within the CNS. Classical features of the disease include impaired vision, nystagmus, dysarthria, ataxia and intention tremor, and weakness/paralysis of one or more limbs. The demyelination is likely due to an autoimmune, inflammatory response that results in the destruction of the myelin sheath covering the axon of the peripheral nerves in the CFS.

The most common form of the disease is episodic. Symptoms develop with subsequent recovery, followed by another attack. In approximately 50 percent of all patients with MS, attacks become more frequent, usually with a worsening of symptomatology. In 30 percent, the disease develops into what is referred to as "progressive/relapsing," the most severe form of the disease. In this state remissions are rare and patients frequently become wheelchair bound.

The diagnosis of MS remains problematic, and frequently the disease is not diagnosed until the patient has experiences two or more "attacks." To aid the clinician, the only laboratory test available is testing the cerebrospinal fluid for oligoclonal bands, present in approximately 90 percent of all patients. Examination of the brain for demyelinating plaques, using magnetic resonance imaging (MRI) is useful but expensive and is not warranted except in a small group of patients in which all other clinical and laboratory tests are negative.

There is no diagnostic laboratory test to determine if a patient is having an "attack," to monitor the progress of the "attack," to determine if the patient is progressing to a more active form of the disease (i.e., progressive/relapsing), nor is any laboratory test available as a prognostic indicator and/or to monitor therapy if administered.

Chronic Fatigue Syndrome (CFS) is an illness of unknown etiology. CFS is often associated with sudden onset, flu-like symptoms, debilitating fatigue, low-grade fever, myalgia and neurocognitive dysfunction. CFS patients typically display reduced Karnofsky Performance (KPS) scores. The KPS measures an individual's ability to function and carry on normal activities. KPS scores range from zero (0) for a completely nonfunctional or dead patient to one hundred (100) for a completely normal function.

Diagnosis of CFS remains one of exclusion. An accumulating body of evidence suggests that CFS is associated with dysregulation of both humoral and cellular immunity, including mitogen response, reactivation of viruses, abnormal cytokine production, diminished natural killer cell function and changes in intermediary metabolites.

It has been suggested that the clinical and immunological abnormalities observed in MS and CFS might be caused by defects in the interferon-inducible pathways i.e., the 2'-5'-oligoadenylate (2-5A) synthetase/RNase L and p68 kinase (PKR) antiviral defense pathways (Suhadolnik et al., Clin. Infect. Dis. 18:S96-S104, 1994; Suhadolnik et al., In Vivo 8:599-604, 1994). The 2-5A synthetase/RNase L pathway is part of the antiviral defense mechanism in mammalian cells (Lengyel, Ann. Rev. Biochem. 51:251-282, 1982; Sen et al., Adv. Virus Res. 42:57-102, 1993).

When activated by dsRNA, 2-5A synthetase converts ATP to 2'-5'-linked oligoadenylates with 5' terminal phosphates. Biologically active 2-5A binds to and activates a latent endoribonuclease, RNase L, which in turn hydrolyzes single-stranded cellular and viral RNA, primarily after UpNp sequences, thereby inhibiting protein synthesis. In addition, circulating white blood cells from patients with CFS have been demonstrated to contain abnormal, low molecular weight forms of RNase L (Suhadolnik et al., J. Interferon & Cytokine Res. 17:377-385, 1997; De Meirleir et al., Am. J. Med. 108:99-105, 2000).

The use of interferon (e.g., Roferon®, Betaseron®) or IFN-inducers (e.g., Ampligen®, Imiquimod®, etc.) as therapy for chronic immune diseases, in particular MS, has met with limited success. For interferon to induce its enzymatic pathways within the cells of the immune system, interferon must first bind to its receptor which in turn activates one of the STAT (signal transducers and activators of transcription) proteins. Indeed STATs were discovered through the study of interferon signaling. A unique feature of Stat-mediated signaling is that the pathway from cell membrane to nucleus is traversed by a single molecule, as opposed to a cascade of kinases and adaptor molecules (Hoey et al., Current Opinion in Genetics and Development 8:582-587, 1998).

Stat-1 plays an important role in growth arrest, in promoting apoptosis and is implicated as a tumor suppressor (Bromberg et al., Oncogene 19:2468-2473, 2000). Stat-1 null cells are resistant to apoptotic induction by TNF-alpha, and re-introduction of Stat-1 restored both TNF-alpha-induced apoptosis and the expression of caspases 1, 2, and 3. (Kumar et al., Science 278:1630-1632, 1997). A wide variety of viruses are known to encode proteins that specifically inhibit the activation of the IFN-mediated state and/or interact with specific IFN-induced proteins causing a disruption of the IFN-mediated state (Alcami et al., Trends in Microbiology 8:410-418, 2000).

Stat-1 deficient mice exhibit a severe defect in IFN-dependent immune responses against viruses and microbial pathogens. Treatment of normal macrophages with IFN-alpha or IFN-gamma in the presence of LPS induced the secretion of nitric oxide (NO). In contrast, IFN-induced NO production was not observed in Stat-1 knockout macrophages. Therefore defective macrophage activity led to a high sensitivity to viral infections. (Durbin et al., Cell 84:443-450, 1996; Meraz et al., Cell 84:431-442, 1996).

If Stat-1 is disabled or otherwise inactive in the cells of the immune system, treatment with interferon or interferon inducer will not be effective in promoting and establishing the interferon-inducible antiviral and antiproliferative pathways.

As the above discussion demonstrates, currently employed methods of diagnosing and/or characterizing MS or CFS disease activity in a subject are inadequate. As such, there is a continued need in the field to develop additional means for diagnosing and/or characterizing MS or CFS disease activity in a subject. Of particular interest would be the development of methods that can be used to predict the effectiveness of a given proposed treatment protocol. In addition, an effective cure for either MS or CFS has yet to be developed. As such, there is continued interest in the identification of new treatment protocols for chronic immune diseases, and particularly for MS and CFS, as well as the development of methods to make interferon based protocols more effective.

Relevant Literature

U.S. patents of interest include: U.S. Pat. Nos. 5,766,859; 5,776,690; 5,830,668; 5,853,996, 5,985,565, 6,153,591, and 6,184,210. Also of interest is WO 91/00097. Other references of interest include: Komaroff, Am. J. Med. 108:69-71, 2000; Yokosawa et al., Arch. Virol. 143:1985-1992, 1998; King et al., J. Biol. Chem. 273:8699-8704, 1998; Hoi-Tao et al., EBMO J. 16:1291-1304, 1997; Bottrel et al., Antimicrob. Agents. Chemother. 43:856-861, 1999; Yang et al., Proc. Natl. Acad. Sci. 97:13631-13636, 2000.

SUMMARY OF THE INVENTION

Methods are provided for characterizing chronic immune disease activity in a subject. In the subject methods, a sample is obtained from a subject suspected of having or known to have a chronic immune disease. The sample is then assayed for the presence and amount of intact (i.e., native) Stat-1 protein and/or fragments thereof. The assay results are used to diagnose the presence of chronic immune disease and/or characterize chronic immune disease activity in a subject. In addition, the assay results may used to evaluated the effectiveness of a given treatment protocol, e.g., to determine whether or not to treat the subject with interferon and/or inducers of interferon. Also provided are methods of treating chronic immune disease via enhancement of Stat-1 activity. Also provided by the subject invention are kits for practicing the methods.

DESCRIPTION OF THE SPECIFIC EMBODIMENTS

Figure 1:
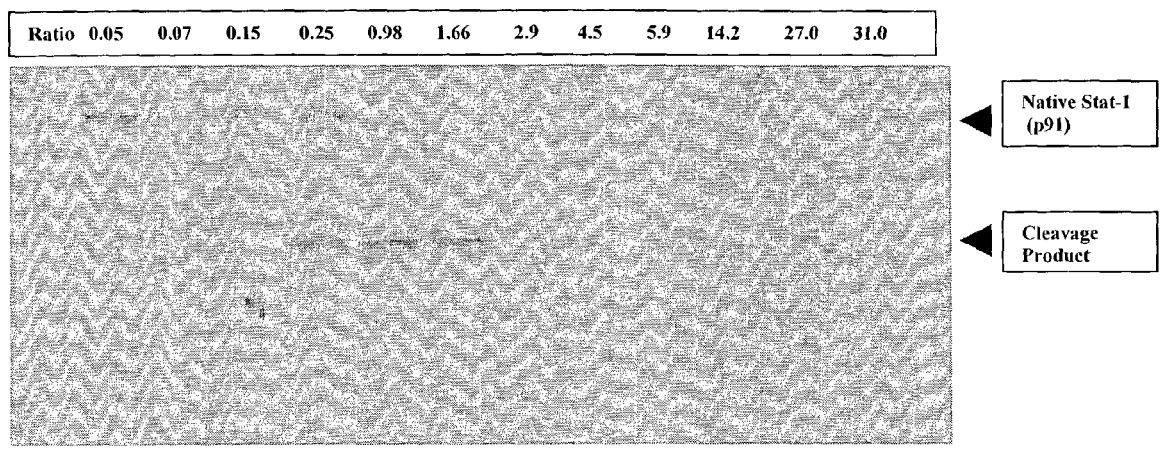
FIG. 1 represents a densitometric scan of a Western blot detecting Stat-1 protein and Stat-1 protein fragments from PBMC extracts from CFS patients. The value indicated at the top of each lane is the ratio of RNase L fragments as calculated by [(LMW/HMW)*10] as assayed in PBMC extracts from CFS patients.

Methods are provided for diagnosing and/or characterizing chronic immune disease activity in a subject. In the subject methods, a sample is obtained from a subject suspected of having or known to have a chronic immune disease. The sample is then assayed for the presence of native Stat-1 protein and/or any lower molecular weight fragments of Stat-1 protein present. The assay results are used to diagnose the presence of chronic immune disease activity and/or characterize chronic immune disease activity in the subject, e.g., to confirm an initial chronic immune disease diagnosis, to determine the stage of the disease, to monitor disease progression, to predict disease attacks, and the like. In certain embodiments, the assay results are also used to predict the effectiveness of a particularly treatment protocol, e.g., to determine whether an interferon based treatment protocol will be effective. In addition, methods of Stat-1 based methods of treating chronic immune disease conditions are provided. Also provided by the subject invention are kits for practicing the methods.

Before the invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components which are described in the publications which might be used in connection with the presently described invention.

As summarized above, the subject invention provides a method of diagnosing the presence of a chronic immune disease in a host. In other words, the subject invention provides a means for determining whether a host is suffering from a chronic immune disease. Specifically, the subject invention provides a method of determining whether a host is suffering from MS or CFS. MS and CFS are disease conditions known to those of skill in the art, and are further defined above and below.

In determining whether a host suffers from a chronic immune disease, a sample from the host is assayed for the presence of one or more low molecular weight fragments of Stat-1 protein (or Stat-1). By low molecular weight Stat-1 fragment is meant a polypeptide that has a sequence of amino acid residues found in full length Stat-1, where this sequence is at least about 10, usually at least about 20 and more usually at least about 50 residues long and is often longer, where the polypeptide has a molecular weight that is less than that molecular weight of full length Stat-1, i.e., where the polypeptide has a molecular weight that is less than about 90 kDa, as measured by SDS-PAGE (see the Experimental Section, infra.) Specifically, the sample is assayed for low molecular weight Stat-1 fragments ranging in weight from about 15 to 75 kDa, usually from about 30 to 60 kDa and more usually from about 45 to 50 kDa. Of particular interest is the identification of a Stat-1 fragment having a molecular weight of about 50 kDa as determined by SDS-PAGE. Representative samples and assay methods for identifying the presence of, and amounts of, low molecular weight Stat-1 fragments are described in greater detail infra.

The presence or absence of the low molecular weight Stat-1 fragments is then used to diagnose whether or not the host suffers from the chronic immune disease. In other words, the presence or absence of low molecular weight Stat-1 fragments in the sample is used to determine whether or not the host suffers from a chronic immune disease, such as CFS or MS. For example, in one embodiment, the presence of one or more low molecular weight Stat-1 fragments is used to determine whether the host suffers from CFS. Likewise, in another embodiment, the presence of one or more low molecular weight Stat-1 fragments is used to determine whether a host suffers from MS. As part of the diagnosis, one may also evaluate the subject for other symptoms of the disease of interest which is to be diagnosed, e.g. the MS or CFS symptoms described in the background section, supra, as well as in other parts of this application.

Also provided by the subject invention are methods of characterizing the chronic immune disease activity, e.g. CFS or MS disease activity, in a subject suspected of having, or known to have, a chronic immune disease, e.g. CFS or MS. Subjects suspected of having, or known to have, a chronic immune disease and thus amenable to the subject methods can be identified using any convenient protocol. One convenient protocol is diagnosis based on clinical symptoms. A number of different clinical symptoms may be used to identify subjects that may have or have the chronic immune disease of interest, where the specific symptoms employed will necessarily depend on the specific chronic immune disease. For example, where the chronic immune disease of interest is CFS, clinical symptoms of interest include: fatigue of six months or longer that causes a reduction in effort of greater than 50 percent of normal output, athralgia, myalgia, sore throat accompanied by swollen glands, cognitive dysfunction (e.g. memory loss); and the like. For MS, clinical symptoms include: weakness of the limbs; sensory symptoms, e.g. paresthesia or hypesthesia; ataxia; optic neuritis; diplopia; trigeminal neuralgia; facial paralysis; vertigo; urinary or bowel movement abnormalities; and cognitive dysfunction, e.g. memory loss, impaired attention, problem-solving difficulties, slowed information processing, and difficulty in shifting between cognitive tasks. The presence of one or more of the above symptoms may be used to identify subjects suspected of suffering from CFS or MS, respectively. Other assays may also be employed, including MRI imaging, the oligoclonal band assay described in greater detail infra, etc.

The first step of the subject methods is to obtain a suitable sample from the subject or patient of interest, i.e. a patient suspected of having or known to have the chronic immune disease of interest, e.g. CFS or MS. The sample is derived from any initial source that contains native Stat-1 and the low molecular weight Stat-1 fragments (if present). Sample sources of interest include, but are not limited to, many different physiological sources, e.g. CSF, urine, saliva, tears, tissue derived samples, e.g. homogenates, and blood or derivatives thereof.

In many embodiments, the sample is derived from cells that comprise the Stat-1 fragments of interest, if present—i.e., if the patient from which the cells are derived has chronic immune disease. In other embodiments, the sample may be derived from fluids into which the proteins of interest have been released, e.g. are present. In many embodiments, a suitable initial source for the patient sample is blood. As such, the sample employed in the subject assays of these embodiments is generally a blood derived sample. The blood derived sample may be derived from whole blood or a fraction thereof, e.g. serum, plasma, etc., where in many embodiments the sample is derived from blood cells harvested from whole blood. Of particular interest as a sample source are mononuclear cells. As such, a preferred sample is one that is derived from peripheral blood mononuclear cells (PBMCs). In certain situations, the sample may be treated to displace Stat-1 fragments from Stat-1 binding proteins, where any convenient treatment protocol may be employed, e.g. acidification, etc.

In these preferred embodiments in which the sample is a PBMC derived sample, the sample is generally a fluid PBMC derived sample. Any convenient methodology for producing a fluid PBMC sample may be employed. In many embodiments, the fluid PBMC derived sample is prepared by: (a) separating PBMCs from whole blood, i.e. collecting PBMCs, e.g. by centrifugation (such as by Ficoll-Hypaque density gradient centrifugation); (b) disrupting the collected cells, e.g. by contacting with a lysing buffer; (c) and removing the resultant cellular debris to obtain a cell-free extract, e.g. by centrifugation. A representative means for producing a suitable fluid PBMC derived sample, i.e. a fluid PBMC extract, is disclosed in WO 98/15646 and U.S. Pat. No. 5,985,565; the disclosures of which is herein incorporated by reference.

Once the patient derived sample is obtained, it is assayed for the presence or absence of one or more low molecular weight Stat-1 fragments, either directly or indirectly. The low molecular weight Stat-1 fragments of interest are those having a molecular weight ranging from about 15 to 75 kDa, usually from about 30 to 60 kDa and specifically of about 45 to 50 kDa, as determined under SDS-PAGE reducing conditions, as described above, with the specific fragment of interest being the 50 kDa fragment.

The sample may be assayed for the presence or absence of the low molecular weight Stat-1 fragments using any convenient methodology. In many embodiments, such methodology involves the following two steps: (a) fractionation of the sample in a manner sufficient such that the one or more Stat-1 fragments and the native Stat-1 (if present) are present in different fractions, i.e. separating the low molecular weight fragments from each other and from the native Stat-1; and (b) detection of the low molecular weight fragments in the specific fractions, i.e. assaying each fraction for the presence or absence of a Stat-1 fragment, where the detection may be qualitative, semi-quantitative or quantitative, and is usually at least semi-quantitative (i.e. not just qualitative).

In these embodiments, fractionation may be accomplished using any convenient methodology. The fractionation technique employed may or may not employ native or non-denaturing conditions. Whether fractionation is carried out under denaturing or non-denaturing conditions depends on the particular manner in which the low molecular weight fragments are detected, e.g. whether or not a non-denatured form is required for detection, where representative detection methods are described in greater detail below. Typically, the non-denaturing conditions are 'native' conditions. By 'native' conditions is meant fractionation by a process that substantially preserves the conformation and folding of the low molecular fragment species in the sample. Native conditions are those conditions that do not denature proteins. A variety of non-denaturing fractionation means are known to those of skill in the art, where one means of interest is gel filtration high performance liquid chromatography. Alternatively, fractionation may be carried out under non-native, e.g. denaturing conditions, such as SDS-PAGE (sodium dodecylsulfate-polyacrylamide gel electrophoresis). As the fractionating step involves separating the various low molecular weight Stat-1 fragments, fractionation results in the production of one or more fractions that putatively contain the low molecular Stat-1 fragment (i.e. is suspected of containing a low molecular weight fragment).

As discussed above, the sample or fraction(s) thereof are assayed for the presence or absence of low molecular weight Stat-1 fragments, where the assay may be a direct assay or an indirect assay. By direct assay is meant an assay that provides for a direct detection of low molecular weight Stat-1 fragments, e.g., an assay that yields direct information regarding the presence and often amount of low molecular weight Stat-1 fragments in a sample, such as an assay where an Stat-1 specific antibody is employed to detect low molecular weight Stat-1 fragments in an appropriately fractionated sample. By indirect assay is meant an assay that detects the presence or absence of low molecular weight Stat-1 fragments through detection, usually quantitation, of another species, e.g. native Stat-1 and total Stat-1 species (e.g., where a relative amount of native Stat-1 to total Stat-1 species in a sample is determined, from which the presence of low molecular weight Stat-1 fragments is indirectly determined). As such, the assay employed may or may not also include a determination of the amount of native or full length Stat-1, i.e. Stat-1 having a molecular weight of approximately 90 kDa in the sample. For example, one can relate an absence of Stat-1 native protein to the presence of Stat-1 fragments.

Any convenient assay protocol may be employed. Suitable assays that may be employed include antibody-based assays, e.g. Western blot assays, such as those described in the experimental section infra. Antibody based assays require the use of antibodies specific for the Stat-1 fragments and/or native Stat-1. The assays may be direct assays, i.e., those which employ antibodies specific for low molecular weight Stat-1 fragments. Alternatively, the assays may be indirect assays, i.e., those which detect native Stat-1 and total amounts of Stat-1 species in a sample, e.g., an assay in which an antibodies specific for the C- and N-termini of the native Stat-1 are employed.

Antibodies that specifically bind to the subject Stat-1 protein and low molecular weight fragments thereof can be prepared using a variety of convenient methods known to those of skill in the art. See Guide to Protein Purification, supra, as well as Antibodies, A Laboratory Manual (Harlow & Lane eds., Cold Spring Harbor Press, 1988). The antibodies may be polyclonal or monoclonal antibodies depending on the nature of the intended use, as long as they are specific for one or more forms of Stat-1 or fragments thereof of interest.

For preparation of polyclonal antibodies, the first step is immunization of the host animal with Stat-1 or an immunogenic fragment, including fragment derivative thereof, where the Stat-1 immunogen will preferably be in substantially pure form, comprising less than about 1% contaminant. Purified Stat-1 or fragments thereof may be obtained using any convenient protocol, including that described in U.S. Pat. No. 6,030,780, the disclosure of which is herein incorporated by reference. The immunogen may comprise complete Stat-1, fragments or derivatives thereof. To increase the immune response of the host animal, the immunogen may be combined with an adjuvant, where suitable adjuvants include alum, dextran, sulfate, large polymeric anions, oil & water emulsions, e.g. Freund's adjuvant, Freund's complete adjuvant, and the like. The immunogen may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The immunogen is administered to the host, usually intradermally, with an initial dosage followed by one or more, usually at least two, additional booster dosages. Following immunization, the blood from the host is collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for Stat-1 and fragments thereof is to immunize a suitable host, where suitable hosts include rats, hamsters, mice and the like, and are preferably mice. The Stat-1 immunogen, which as above, may be the entire Stat-1 protein or a fragment or derivative thereof, is administered to the host in any convenient manner, where such methods include: subcutaneous injection with adjuvants, nitrocellulose implants comprising the immunogen, intrasplenic injections, and the like, where the immunization protocol may be modulated to obtain a desired type of antibody, e.g. IgG or IgM, where such methods are known in the art. Following immunization, plasma cells are harvested from the immunized host, where sources of plasma cells include the spleen, lymph nodes and the like, with the spleen being preferred. The plasma cells are then immortalized with myeloma cells to produce hybridoma cells. A variety of myeloma cell lines are available and known to those of skill in the art. The plasma and myeloma cells are fused by combining the cells in a fusion medium usually in a ratio of about 10 plasma cells to 1 myeloma cell, where suitable fusion mediums include a fusion agent, e.g. PEG 1000, and the like. Following fusion, the fused cells are selected, e.g. by growing on HAT medium. Following hybridoma cell production, culture supernatant from individual hybridomas is screened for reactivity with Stat-1 using standard techniques, where such screening techniques include ELISA, dot blot immunoassays and the like. The antibody may be purified from the supernatants or ascites fluid by conventional techniques, e.g. affinity chromatography Stat-1 bound to an insoluble support, protein A sepharose and the like.

Antibodies specific for Stat-1 and fragment thereof are known in the art, and include those specific antibodies described in U.S. Pat. No. 6,030,780; the disclosure of which is herein incorporated by reference.

The above prepared or obtained antibodies may be modified in a number of different ways to optimize their utility for use in a particular immunoassay. For example, antibody fragments, such as Fv, F(ab)$_2$ and Fab may be prepared by cleavage of the intact protein, e.g. by protease or chemical cleavage.

The antibodies, fragments or derivatives thereof may also be labeled in order to facilitate detection. A variety of protein labeling schemes are known in the art and may be employed, the particular scheme and label chosen being the one most convenient for the intended use of the antibody, e.g. immunoassay. Examples of labels include labels that permit both the direct and indirect measurement of the presence of the antibody. Examples of labels that permit direct measurement of the antibody include radiolabels, such as $^3$H or $^{125}$I, fluorescers, dyes, beads, chemilumninescers, colloidal particles, and the like. Examples of labels which permit indirect measurement of the presence of the antibody include enzymes where a substrate may provide for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g. the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. See also the methods of labeling Stat-1 (and Stat-1 fragment) specific antibodies disclosed in U.S. Pat. No. 6,030,780; the disclosure of which is herein incorporated by reference.

In immunoassays of the subject invention, a number of different immunoassay formats are known in the art and may be employed. Representative assay formats include Western blots on protein gels or protein spots on filters, where the antibody is labeled as described above, as is known in the art. For a representative example of a Western blot assay for the presence of Stat-1 and fragments thereof in a sample, see the experimental section infra.

Other immunoassays include those based on competitive formats, as are known in the art. One such format would be where a solid support is coated with Stat-1. Labeled antibody is then combined with the patient derived sample suspected to produce a reaction mixture which, following sufficient incubation time for binding complexes to form, is contacted with the solid phase bound Stat-1. The amount of labeled antibody which binds to the solid phase will be proportional to the amount of Stat-1 or fragments thereof in the sample, and the presence of Stat-1 and fragments thereof may therefore be detected. Other competitive formats that may be employed include those where the sample suspected of comprising Stat-1 fragments is combined with a known amount of labeled Stat-1 fragments and then contacted with a solid support coated with antibody specific for Stat-1 fragments. Such assay formats are known in the art and further described in both Guide to Protein Purification, supra, and Antibodies, A Laboratory Manual, supra. Sandwich-format assays may also be employed. A sandwich assay is performed by initially attaching a first of the two types of antibodies to an insoluble surface or support. This first antibody may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently. The insoluble supports may be any compositions to which antibodies or fragments thereof can be bound, which is readily separated from soluble material, and which is otherwise compatible with the overall method of measuring Stat-1 in the sample. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples. Before adding patient samples or fractions thereof, the non-specific binding sites on the insoluble support i.e. those not occupied by the first antibody, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used. Samples, fractions or aliquots thereof are then added to separately assayable supports (for example, separate wells of a microtiter plate) containing support-bound allergen. Preferably, a series of standards, containing known concentrations of Stat-1 is assayed in parallel with the samples or aliquots thereof to serve as controls. Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for Stat-1 molecules to bind the insoluble first antibody. Generally, from about 0.1 to 3 hr is sufficient, usually 1 hr sufficing. After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample. After washing, a solution containing the second Stat-1 or Stat-1 fragment specific antibody is applied. The second antibody may be labeled, as described above, to facilitate direct, or indirect detection and/or quantification of binding. Examples of labels which permit direct measurement of immunocomplexes include radiolabels, such as $^3$H or $^{125}$I, fluorescers, dyes, beads, chemilumninescers, colloidal particles, and the like. Examples of labels which permit indirect measurement of binding include enzymes where the substrate may provide for a colored or fluorescent product. In a preferred embodiment, the second antibody is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Alternatively, the antibody may be unlabeled. In this case, a labeled second receptor-specific compound is employed which binds to the second antibody. Such a second receptor-specific compound can be labeled in any of the above manners. It is possible to select such compounds such that multiple compounds bind each molecule of bound second receptor. Examples of second antibody/second receptor-specific molecule pairs include antibody/anti-antibody and avidin (or streptavidin)/biotin. Since the resultant signal is thus amplified, this technique may be advantageous where only a small amount of Stat-1 or fragment thereof is present. An example is the use of a labeled antibody specific to the second antibody. The volume, composition and concentration of second antibody solution provides for measurable binding to the Stat-1 already bound to the first antibody. Generally, the same volume as that of the sample is used: from about 0.001 to 1 ml is sufficient, usually about 0.1 ml sufficing. The concentration will generally be sufficient to saturate all Stat-1 potentially bound to first antibody. The concentration generally will be about 0.1 to 50 µg/ml, preferably about 1 µg/ml. The solution containing the second antibody is generally buffered in the range of about pH 6.5-9.5. The solution may also contain an innocuous protein as previously described. The incubation time should be sufficient for the labeled ligand to bind available molecules. Generally, from about 0.1 to 3 hr is sufficient, usually 1 hr sufficing. After the second antibody has bound, the insoluble support is generally again washed free of nonspecifically bound second receptor, essentially as described for prior washes. After nonspecifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490-495 nm is conveniently measured with a spectrophotometer.

Depending on the particular nature of the antibody based assay employed, it may be desirable to employ antibodies that are capable of distinguishing between the various Stat-1 forms and fragments thereof. For example, in a Western blot assay a single type of antibody that recognizes all of the various Stat-1 fragments and the native Stat-1 itself may be employed, since the various fragments and native protein are pre-separated, e.g. by gel electrophoresis. However, where the various fragments and native protein are not separated prior to detection, e.g. in the competitive and sandwich assays described above, it is desirable to use a plurality of antibodies which are capable of specifically recognizing only a single Stat-1 species of interest, with substantially no cross-reactivity with other Stat-1 species or fragments that may be present in the sample.

In the subject methods, the sample or fractions thereof are at least assayed for the presence or absence of the low molecular Stat-1 fragments or species, and often times the native species as well, where the assay may be a direct assay for low molecular weight fragments or an indirect assay for low molecular weight fragments, as indicated above. In some embodiments, qualitative results are sufficient. Thus, one may be interested in identifying the presence or absence of the low molecular weight Stat-1 fragments as a marker for the chronic immune disease, e.g. in the diagnostic methods described above. Alternatively, one may be interested in making a qualitative determination of the ratio of the low molecular weight species to the native species. In many embodiments, the assays employed at least provide semi-quantitative detection of the various molecular weight Stat-1 species, and not just qualitative detection.

In assaying for low molecular weight Stat-1 fragments or species in the subject methods, one may look for: (a) the presence or absence of the low molecular weight fragments; (b) the pattern of the low molecular weight fragments and, optionally full length Stat-1 (where by pattern is meant the presence of each fragment and, optionally relative amount of each fragment); (c) the ratio of the amounts of the various low molecular weight species to each other and/or to the full length Stat-1; and the like; (d) the relative amount of high molecular weight or native Stat-1 to all Stat-1 species in the sample; etc.

In many embodiments, based on the presence or absence of the various molecular weight Stat-1 species, and usually the semi-quantitative values obtained for each of the species of interest, the chronic immune disease activity in the subject from which the sample was derived is characterized. This broad category of embodiments includes those in which the low molecular weight Stat-1 species are directly assayed, e.g., those methods where: (a) the simple presence or absence of low molecular weight species is used to characterize the disease; (b) the ratio of low molecular weight species to high molecular weight species is used to characterize the disease; and (c) the pattern or amounts of two or more different low molecular weight species is used to characterize the disease; etc.

In yet other embodiments, e.g. those based on assays which indirectly determine the presence or absence of low molecular weight Stat-1 species, the relative amounts of the various Stat-1 species in the sample to each other, e.g., the relative amount of native or high molecular weight Stat-1 to the total amount of Stat-1, i.e., native Stat-1 and fragment species thereof, in the sample is used to characterize the chronic immune disease activity in the subject.

Characterization of chronic immune disease activity according to the subject methods typically involves comparing the results obtained to a table or other source of predetermined values or reference values which provide information about the disease activity in the host, e.g. that positively or negatively correlate to the presence of the chronic immune disease, a particular stage of the chronic immune disease, and the like. For example, a table of values may be consulted in this step, where the table comprises representative values for the high and low molecular weight proteins as found in patients suffering from the chronic immune disease of interest. The values may be presented in numerical form, in picture form (e.g. as bands on a gel), and the like. By comparing the observed values with these reference values, e.g. by comparing a pattern of the Stat-1 species in the sample to a reference pattern or picture, characterization of the disease activity, e.g. confirmation of diagnosis, determination of disease state, etc., is readily made. In other embodiments, the ratio of two or more of the different species and/or full length Stat-1 is then compared to reference list of ratios to characterize the chronic immune disease activity.

As summarized above, the subject methods are methods of characterizing chronic immune disease activity in a host. The term characterizing is used broadly to refer to derivation of any type of information about the state of the chronic immune disease in the host. As such, the subject methods may be used to confirm an initial diagnosis of chronic immune disease, to determine the state of the disease in a patient known to have the chronic immune disease, to monitor the progression of the disease, to predict the occurrence of an attack, and the like. Where the subject invention is employed to confirm an initial diagnosis, a sample is obtained from subject suspected of having the chronic immune disease (where the subject may be identified as described supra). For example, the sample is assayed for the presence of the high and low molecular weight Stat-1 species, a ratio of the two species is derived and then compared to reference values, where the reference values correlate given ratios to the presence or absence of the chronic immune disease.

The subject methods are also employed to determine the stage of the chronic immune disease in the subject. In other words, the subject chronic immune disease activity characterization methods may be employed to determine whether the patient is in a remission stage, a chronic stage etc. For example, the subject methods may be employed to determine whether an MS patient is in the relapsing-remitting stage or in the chronic progressive stage of the disease. To determine the stage of the disease, the observed values for the one or more Stat-1 species, and ratios where desired, in the assayed sample are compared to reference values that are correlated to a particular stage of chronic immune disease, e.g. remitting relapsing or chronic progressive stage of MS.

In yet other embodiments, characterization of disease activity yields information concerning the disease progression in the patient, e.g. whether disease progression has accelerated or slowed. For example, the initial characterization date, i.e. the amount of high (i.e., native) and low molecular weight forms of Stat-1 in the patient derived sample could be employed as a baseline value to evaluate subsequent testings, e.g. at some time following the initial testing, e.g. 3 months. If the amount of low molecular weight form decreases in subsequent testing, this indicates that the disease is not progressing. Alternatively, if the amount of low molecular weight form increases, this indicates that the disease is progressing in severity.

The characterization data obtained from the subject methods may also be used to determine whether a particular therapeutic regimen is having positive affects with respect to the progression of the disease. For example, at various time periods during the course of treatment, the subject methods may be performed to obtain a reading of the amount of high and low molecular weight forms of the Stat-1 species of interest. If the amount of the low molecular weight marker is increasing, this indicates that the treatment regimen is not having the desired effect. Alternatively, if the amount of the low molecular weight marker is decreasing, this indicates that the treatment regimen is working.

In yet other embodiments, the characterization data obtained from the subject methods is used to predict when a chronic immune disease attack, e.g. MS attack, may occur. In this embodiment, the characterization data is compared to reference values, where some of the reference values correlate to the occurrence of an attack.

Depending on the particular test protocol, the subject methods may further include one or more additional assays associated with the chronic immune disease of interest. For example, one may couple the subject methods with assays that look for the presence of low molecular weight proteins that exhibit RNase L activity, the ratio of high to low molecular weight proteins that exhibit RNase L activity, etc., as described in U.S. Pat. Nos. 5,985,565; 6,080,554; 6,207,366; and 6,214,544 the disclosures of which are herein incorporated by reference. Other representative assays of interest include biochemical assays capable of identifying MS activity in the subject, e.g. assays which detect the presence of oligoclonal bands in cerebral spinal fluid (CSF). A variety of such assays are known to those of skill in the art and may be employed in the subject methods. See e.g. Mehta et al., Electrophoresis 9:126-8, 1998; Mehta et al., J Clin Lab Immunol. 6:17-22, 1981; Trbojevic-Cepe et al., Neurologija. 38:11-21, 1989; Lasne et al., J Neurochem. 36:1872-4, 1981; Mehta et al., J Neurosci Methods 16:277-82, 1986.

Also provided by the subject invention are kits for use in carrying out the subject methods. The kits at least comprise reagents necessary for carrying out the Stat-1 species detection assays, where such kits may include: Stat-1 specific antibodies and/or immunoassay devices comprising the same; members of a signal producing system, such as antibodies, enzyme substrates, and the like; various buffers for use in carrying out the subject detection assays; and the like. The kits may further include one or more reagents necessary for preparation of the patient derived sample, such as heparin, Ficoll-Hypaque, lysing buffer, protease inhibitor, and the like, e.g. where the patient sample is PBMC derived, etc. In addition, the subject kits may further include one or more components employed in fractionation of the sample, such as an electrophoretic medium or precursors thereof, e.g. dried precursors of polacrylamide gels, one or more buffer mediums or components thereof, and the like. In most embodiments, the kits further include at least an information storage and presentation medium that contains reference data with which assay results may be compared in order to diagnose and/or characterize the chronic immune disease activity in the subject being assayed, i.e. reference data that includes various values of the high and low molecular weight Stat-1 species and relates these values to the presence or absence of chronic immune disease and/or the activity of the disease in the host. The information storage and presentation medium may be in any convenient form, such as a printed information on a package insert, an electronic file present on an electronic storage medium, e.g. a magnetic disk, CD-ROM, and the like. In yet other embodiments, the kits may include alternative means for obtaining reference data, e.g. a website for obtaining the reference data "on-line." The kits may further include means for obtaining the patient sample, e.g. a syringe. The subject kits further typically include instructions for carrying out the subject methods, where these instructions may be present on a package insert and/or the packaging of the kit. Finally, the kit may further include one or more reagents from an additional biochemical assay which is used to detect the presence of and/or characterize the chronic immune disease of interest. For example, where MS is the chronic immune disease of interest, the kits may further include one or more reagents from an assay designed to detect the presence of oligoclonal bands in CSF, e.g. immunoxification reagents (e.g. anti-IgG); labeling reagents, such as silver salts, and the like.

Also provided by the subject invention are assay methods for use in detecting the proteolytic activity of a sample with respect to direct cleavage of native Stat-1 protein and/or recombinant Stat-1 protein. In these assay methods of the subject invention, a subject sample, as described above, is contacted with a source of native and/or recombinant Stat-1 protein under conditions sufficient for Stat-1 protein cleavage products to be generated if the sample comprises the proteolytic activity of interest. Generally, contact is maintained for a period of time sufficient for a representative amount of cleavage products to be produced, where this incubation time typically ranges from about 5 to 120 minutes, usually from about 30 to 60 minutes. The source of native Stat-1 protein and/or recombinant Stat-1 protein that may be used in these assays may be any convenient source. As such, the source may be a naturally occurring source, a recombinant source and the like.

Any convenient cleavage product detection format may be employed. Depending on the detection format employed, the source of native and/or recombinant Stat-1 protein may or may not be labeled. For example, one convenient assay employs the use of substrate bound native and/or recombinant Stat-1, where the proteins are labeled, generally proximal to or at the end of the protein that is not attached, either directly or indirectly, to the substrate. The substrate bound protein is then contacted with the sample, as described above, and, following incubation, any cleavage products, e.g. low molecular weight Stat-1 cleavage products, are detected. Non-labeled protocols may also be employed, e.g. antibody based (such as Western blot formats) as described supra.

Following detection of the cleavage products, the presence of, and generally amount of cleavage products is related to the proteolytic activity of the sample, specifically the Stat-1 proteolytic activity of the sample. In other words, the pattern of native and/or recombinant Stat-1 cleavage products or proteins in the sample is related to the proteolytic characteristics or ability of the sample. For example, the presence of cleavage products indicates that the sample comprises the target proteolytic activity, while the amount of the cleavage products indicates the level of proteolytic activity.

The above assay for proteolytic activity in the sample may be employed in many applications. For example, the above proteolytic activity assay may be employed in addition to, or as a substitute for, the Stat-1 species detection assays in the above described methods of diagnosing and/or characterizing chronic immune disease activity.

Also provided are kits for use in practicing the subject proteolytic activity assays. The subject kits include, among other components, a source of native and/or recombinant Stat-1 (e.g. source of full length recombinant Stat-1 protein), where the source may be stably associated with the surface of a substrate and/or labeled, depending on the nature of the assay to be performed. Generally, the kits will also comprise a medium having reference values recorded thereon for use in interpreting the assay data and relating the data to the proteolytic activity in the sample.

In addition to the diagnostic/characterization applications described above, the above described methods also find use in evaluating the effectiveness of a particular chronic immune disease therapeutic protocol. More specifically, also provided are methods of evaluating whether or not interferon based therapy for chronic immune disease will be effective for a given subject, i.e., whether a particular subject suffering from chronic immune disease will benefit from interferon based therapy (i.e., therapy with interferon or inducers thereof, as described above).

In such methods, the first step is to determine the amount of native or full length Stat-1 in the relevant patient sample, e.g., PBMC, as described above. Based on the amount of native Stat-1 present, the decision is made as to whether or not interferon-based therapy is indicated. More specifically, native Stat-1 present in the sample indicates that interferon based therapy will be effective, while an absence of Stat-1 present in the sample indicates that Stat-1 therapy will not be effective. As such, following detection of the presence or absence of native Stat-1 in the sample, a decision is made as to whether or not interferon based therapy will be effective.

As summarized above, the subject invention also provides methods for treating a host suffering from a chronic immune disease. Specifically, the subject invention provides methods of treating a host suffering from MS or CFS.

In practicing the subject methods, an effective amount of an agent that enhances Stat-1 protein activity, specifically in PBMC, is administered to the host suffering from the chronic immune disease. By enhance is meant that the Stat-1 activity in the host, particularly in PBMC of the host, is increased by at least about 2 fold, usually by at least about 3 fold and more usually by at least about 5 fold, as compared to that observed in a control, i.e., a PBMC from the host that has not been contacted by the active agent(s).

Enhancement of Stat-1 activity can be accomplished in any convenient manner. Particular active agents of interest include, but are not limited to Stat-1 cleavage-inhibitory agents and Stat-1 expression enhancing agents. Each of these types of agents is now described separately in greater detail.

Stat-1 Cleavage-Inhibitory Agents

Stat-1 cleavage-inhibitory agents of interest for use in the subject methods are agents that inhibit cleavage or fragmentation of Stat-1 protein. The target molecule is a protein or activity, e.g., an enzyme that cleaves native Stat-1 protein into fragments. An example of such a protein with Stat-1 cleavage ability is caspase 3 (see King et al., J. Biol. Chem. 273:8699-8704, 1998). By inhibit is meant that these agents at least reduce, if not substantially or completely stop, the cleavage of Stat-1. Stat-1 cleavage-inhibitory agents typically reduce the cleavage or Stat-1 by at least about 2 fold, usually at least about 3 fold and more usually at least about 5 fold. Inhibitors of interest include agents that bind to the target molecule (e.g., protease) and concomitantly reduce its activity, as well as agents that reduce the expression of the target molecule so that the overall cleavage activity of the target molecule is reduced. As such, agents of interest include small molecule agents, as may be identified in the assays described below and antibodies specific to inhibiting the action of the Stat-1 cleaving target molecules. Small molecule agents of interest include small organic compounds having a molecular weight of more than 50 and less than about 2,500 daltons. The small molecule agents comprise functional groups necessary for structural interaction with proteins, particularly hydrogen bonding, and typically include at least an amine, carbonyl, hydroxyl or carboxyl group, preferably at least two of the functional chemical groups. The small molecule agents often comprise cyclical carbon or heterocyclic structures and/or aromatic or polyaromatic structures substituted with one or more of the above functional groups. Small molecule agents of interest are also found among biomolecules including, but not limited to: peptides, saccharides, fatty acids, steroids, purines, pyrimidines, derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling. Protease specific antibodies may be readily produced using the procedures described above.

In yet other embodiments of the invention, the active agent is an agent that modulates, and generally decreases or down regulates, the expression of the Stat-1-specific protease gene in the host. Antisense molecules can be used to down-regulate expression of genes in cells. The antisense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al., Nature Biotechnol. 14:840-844, 1996).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al., supra, and Milligan et al., supra.) Preferred oligonucleotides are chemically modified from the native phosphodiester structure, in order to increase their intracellular stability and binding affinity. A number of such modifications have been described in the literature to alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-$CH_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'—OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al., Nucl. Acids Res. 23:4434-42, 1995). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al., Appl. Biochem. Biotechnol. 54:43-56, 1995.

A further alternative to the above is the use of double-stranded RNA sequences, or the production thereof by introducing vectors for such in the host, the nucleic acid sequences of which are identical to all or part of the Stat-1-specific protease gene. Such a double-stranded RNA is capable of binding to and causing the degradation of the homologous mRNA species. Thus, the mRNA coding for the production of Stat-1-specific protease is targeted for removal by this method. This technique is referred to as RNA interference, examples of which are described in Tuschl et al., Genes and Development 13:3191-3197, 1999, and Zamore, Cell 101:25-33, 2000.

Stat-1 Expression Enhancing Agents

In yet other embodiments of the subject invention, the active agent is a Stat-1 expression-enhancing agent. By Stat-1 expression enhancing agent is meant an agent that enhances expression of native Stat-1 mRNA and/or the production of native Stat-1 protein in the host, particularly in PBMC of the host. Agents of interest include, but are not limited to: Stat-1 nucleic acid and protein therapeutic compositions. In this embodiment, the genes or gene fragments are useful in gene therapy to enhance Stat-1 gene activity. Expression vectors may be used to introduce the Stat-1 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g., plasmid; retrovirus, e.g. lentivirus; adenovirus; and the like, where the vectors are able to transiently or stably be maintained in the cells, usually for a period of at least about one day, more usually for a period of at least about several days to several weeks.

The gene or protein may be introduced into tissues or host cells by any number of routes, including viral infection, microinjection, or fusion of vesicles. Jet injection may also be used for intramuscular administration, as described by Furth et al., Anal. Biochem. 205:365-368, 1992. The DNA may be coated onto gold microparticles, and delivered intradermally by a particle bombardment device, or "gene gun" as described by Tang et al., Nature 356:152-154, 1992, where gold microprojectiles are coated with the DNA and then bombarded into skin cells. The nucleic acid and protein sequence of Stat-1 is known, where the human mRNA and amino acid sequence are deposited in GenBank under Accession no. NM_007315.

Also of interest is the use of agents that modulate the endogenous Stat-1 gene of the host to enhance its expression. For example, the endogenous Stat-1 gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the enhancement of Stat-1 expression without manipulation of the encoding nucleic acid itself, but instead through integration of a regulatory sequence into the genome of cell of the host that already includes a gene encoding the desired protein, as described in the above incorporated patent documents.

Also of interest is the use of agents that modulate the levels of native Stat-1 protein in the host, particularly in PBMC of the host. Such an agent may act directly on the PBMCs of the host, such as one of the interferon class of proteins, or indirectly on the PBMCs through the induction of interferon proteins (see Bottrel et al., Antimicrob. Agents Chemother. 43:856-861, 1999). In such instance where the agent acts to induce the production of interferon, the combination of enhanced expression of Stat-1 protein via gene therapy techniques and the induction of interferon through the administration of such agents as imidazoquinolines, may result in significant therapeutic benefit to the patient.

As mentioned above, in the subject methods an effective amount of one or more of the above described active agents is administered to the host, where "effective amount" means a dosage sufficient to produce a desired result, where the desired result is at least an amelioration, if not complete cessation of the chronic immune disease symptoms.

In the subject methods, the active agent(s) may be administered to the host using any convenient means capable of resulting in the desired treatment. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al., supra. The agent may be coated onto gold microparticles, and delivered intradermally by a particle bombardment device, or "gene gun" as described in the literature as described by Tang et al., supra.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

As mentioned above, by treatment is meant that at least an amelioration of the symptoms associated with the chronic immune disease, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the chronic immune disease condition.

In treating subjects according to the subject invention, the Stat-1 activity enhancing agent may be administered by itself, or in conjunction with one or more additional chronic immune disease therapeutic agents. For example, the Stat-1 activity enhancing agent may be administered in conjunction with an interferon agent, e.g., interferon or an inducer thereof, as described above and in U.S. Pat. No. 6,013,253, the disclosure of which is herein incorporated by reference.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered by way of illustration and not by way of limitation.

Experimental Section

Venous blood was collected from patients with Chronic Fatigue Syndrome, Multiple Sclerosis, and from healthy controls using standard sterile techniques. Patients with CFS as diagnosed by meeting the established case definition were selected from a special clinic at the Free University of Brussels, Brussels, Belgium. Patients with MS as diagnosed by standard procedures were selected from a special clinic in Overpelt, Belgium. Blood from healthy volunteer controls was provided by the Sports Medicine center at the Free University of Brussels, Brussels, Belgium. Patient consent was obtained in all cases.

I. Procedures

A. Cell Isolation and Protein Extraction

Peripheral blood mononuclear cells (PBMCs) were separated from heparinized blood (30 mLs) by Ficoll-Hypaque density gradient centrifugation. The blood was layered onto 20 mLs of Ficoll-Hypaque (Boyum, Scandinavian Journal of Clinical Laboratory Investigation, 97:101-109, 1968) at a density of 1.077 g/mL at 20 C and centrifuged for 30 minutes at 500×g. The PBMC layer was removed and washed once with 5 volumes of phosphate buffered saline (PBS). The cells were then resuspended in 5 mLs of red blood cell lysing buffer (155 mM $NH_4Cl$, 10 mM $NaHCO_3$, 0.1 mM EDTA, pH 7.4), kept on ice for 5 minutes, then centrifuged for 5 minutes at 500×g. The resultant cell pellet was washed once with 15 mLs of PBS and centrifuged for 5 minutes at 500×g. The resultant pellet was then stored at −70 C until the protein extraction procedure could be performed.

To extract the proteins from the cell pellet, PBMCs were resuspended in a volume approximately 5-10 times the packed cell volume in the extract buffer (10 mM HEPES, pH 7.6, 90 mM KCl, 1.5 mM $Mg(OAc)_2$, 0.5% non-ionic detergent (such as Nonidet P-40 or Igepal CA-630, Sigma Chemical Corporation)). The extract buffer also contained a mixture of protease inhibitors to help stabilize the extract and impeded the action of proteases. Once such commercially available mixture is the MiniComplete protease inhibitor cocktail (Boehringer-Mannheim). This contains aprotinin, leupeptin, pefabloc-SC and EDTA.

The extraction procedure was performed at 2-4 degrees C., holding the cell pellet-extraction buffer in ice water or on wet ice for 5 minutes. The cell pellet-buffer mix was then vortexed at medium speed for 2 minutes at room temperature to ensure complete solubilization of the cell membranes. The cell pellet-buffer mix was then placed at 2-4 C for an additional 5 minutes. The final step was to centrifuge the cell pellet-buffer mix at high speed in a microcentrifuge (16,000×g) for 2 minutes. The supernatant containing the proteins of interest was collected and the cell pellet is discarded. All cell extracts were stored at −70 C until further analysis could be performed.

Quantification of protein in the patient cell extracts was performed using a standard commercially available procedure of a modified Bradford method (Bio-Rad Laboratories) following the manufacturer's recommended procedure.

B. Quantification of 2'-5'A Binding Proteins

Analysis of LMW and HMW 2'5'A binding proteins was performed using a radiolabeled 2'-5'A trimer and SDS-PAGE as described by the method of Charachon et al. (Biochemistry 29:2550-2556, 1990). Briefly, 2'-5'A trimer was radiolabeled by the ligation of $^{32}$P-pCp to the 3' end (method of Charachon). After removal of the 3' terminal phosphate by treatment with bacterial alkaline phosphatase, the 3' ribose residue of pC was oxidized with sodium metaperiodate (10 mM final concentration, pH 4.75) for one hour at 4 C to form 2'5'A-$^{32}$pC-OX. This reaction mixture was subsequently equilibrated to pH 8.0 by the addition of NaOH. This oxidized molecule was used as the radiolabel in all subsequent reactions for RNase L protein analysis (referred to below as radiolabeled 2'5'A).

The radiolabeled 2'5'A was incubated with 200 micrograms of cell extract at 2-4 C for 15 minutes to allow the radiolabeled 2'5'A to interact with any 2'5'A-binding proteins present, such as RNase L (all molecular weight species). The 2'-5'A radiolabel was then covalently attached to all RNase L species by the addition of cyanoborohydride (20 mM in 100 mM phosphate buffer, pH 8.0). The reduction reaction was allowed to occur for 20 minutes at room temperature. SDS-PAGE sample buffer, including a tracking dye, was added to the samples and all samples were incubated at 95 C for 5 minutes to reduce any disulfide bonds present.

The samples were then subjected to standard SDS-polyacrylamide gel electrophoresis using a 4 percent stacking gel and a 10 percent separating gel (Bisbal et al, European Journal of Biochemistry 179:595-602, 1989). Also included in the first lane of each gel was a molecular weight marker, pre-stained to be visible as it migrated during the course of electrophoresis (Bio-Rad Laboratories). The gel was electrophoresed until the tracking dye had migrated to the bottom of the gel (approximately 5 hours at a constant current of 30 mAmps). The gel was then dried and subjected to autoradiography (Bio-Rad Laboratories FX Imager).

The autoradiographs were then analyzed by densitometry, and quantification of any and all RNase L species present was performed using specialized software (Quantity One from Bio-Rad Laboratories). The results are expressed as the density (or relative amount) of 37 kDa LMW RNase L present divided by the density (or relative amount) of 80 kDa HMW RNase L present, multiplied by a constant factor of 10.

C. Quantification of Stat-1 Protein and Related Fragments by Western Blot

Briefly, the procedure used is as follows: 200 micrograms of protein extracted from the cytoplasm of PBMCs was mixed with 2×SDS-PAGE gel sample dye that included a tracking dye, and heated to 95 C for five minutes to denature the proteins. The denatured samples were then subjected to standard SDS-PAGE using a 4 percent stacking gel and 10 percent separating gel. Also included in the first lane of each gel was a molecular weight marker, pre-stained to be visible as it migrated during the course of electrophoresis (Bio-Rad Laboratories). The gel was electrophoresed until the tracking dye had migrated to the bottom of the gel.

The gel was then transferred to a PVDF membrane (Bio-Rad Laboratories) using a semi-dry transfer system (Amersham-Pharmacia Biotech). Transfer was performed at an average current of 0.8 milliamp per cm2 of gel (or 100 mA for a standard 15 cm×8 cm gel) for two hours. After transfer was complete (as determined by the visual agreement of the transfer of the color from the pre-stained molecular weight markers to the membrane), the membrane was allowed to dry thoroughly at room temperature for at least one hour.

Western blotting was performed using the following format: The membrane was first wet with a minimum volume of 100 percent methanol (according to the manufacturer's instruction). Then a solution of five percent non-fat dry milk (5% NFDM) was used to 'block' the membrane ('blocking buffer') to eliminate non-specific background binding of antibody. The membrane was 'blocked' for one hour with gentle shaking on an orbital shaker.

The blocking buffer was discarded and fresh blocking buffer was added in the amount of approximately 0.1 mL per cm2 of membrane, to which was added the primary antibody (mouse anti-Stat-1 monoclonal antibody; Santa Cruz Biotechnologies, catalog number sc-417) at a 1:100 dilution. The membrane was allowed to react with the primary antibody for one hour with gentle shaking on an orbital shaker. The primary antibody solution was then discarded and the membrane was washed three times with 25 mLs per wash of phosphate buffered saline (PBS, pH=7.4) plus 0.1% Tween 20 (polyoxyethylene sorbitan monolaurate; Sigma Corporation). Each wash was five minutes in length, with shaking, and the each time the solution was discarded.

Fresh blocking buffer was added in the amount of approximately 0.1 mL per cm2 of membrane, to which was added the secondary antibody (goat anti-mouse antibody, conjugated to horseradish peroxidase (GAR-HRP); Bio-Rad Laboratories) at a 1:2000 dilution according to the manufacturer's recommendations. The membrane was allowed to react with the secondary antibody for thirty minutes with gentle shaking on an orbital shaker. The secondary antibody solution was discarded and the membrane was washed three times with 25 mLs per wash of phosphate buffered saline (PBS, pH=7.4) plus 0.1% Tween 20. Each wash was five minutes in length, with shaking, and the each time the solution was discarded.

Color development was performed using the Opti4-CN kit (Bio-Rad Laboratories) according to the manufacturer's recommendations. Color development was allowed to proceed for 15 minutes and the membrane was then rinsed in copious changes of water and allowed to dry at room temperature. The membrane was then analyzed by densitometry and quantification of Stat-1 and Stat-1 fragment proteins present was performed using specialized software (Quantity One from Bio-Rad Laboratories).

As a control to ensure that the disappearance of Stat-1 protein was not due to nonspecific proteolysis resulting in the degradation of all proteins present, Western blotting was performed with anti-Bcl-2 antibody (mouse anti-Bcl-2 monoclonal antibody; Santa Cruz Biotechnologies, catalog number sc-509) at a 1:100 dilution. The amount of PBMC protein extract used and the conditions for SDS-PAGE, transfer to PVDF membrane, Western blotting, color development and densitometry were performed exactly as described above.

D. Effect of Protease Inhibitors on Stat-1 Protein Degradation

To demonstrate the presence of Stat-1-specific proteases in PBMC extracts, two extracts were mixed in the presence or absence of specific protease inhibitors. One of the two extracts used was from a healthy control (i.e., RNase L ratio<0.2; no protease present, detectable levels of Stat-1 protein). The other extract was from a patient with CFS (i.e., RNase L ratio>2.0; protease(s) present, no detectable level of Stat-1 protein).

Sixty (60) micrograms of PBMC extract from the healthy control was mixed with 60 micrograms of PBMC extract from a CFS patient and incubated at 37 C for 15 minutes in the presence of a) buffer only, b) DMSO (solvent for the protease inhibitors), c) Calpastatine, 50 micromolar final concentration, d) Calpain Inhibitor Type I, 200 micromolar final concentration, e) Calpain Inhibitor Type II, 200 micromolar final concentration, f) Caspase 3 Inhibitor Type II, 5 micromolar final concentration, or g) Proteasome Inhibitor (MG 132), 50 micromolar final concentration. All protease inhibitors above, as well as DMSO, were from Sigma Chemical Company.

After the 15 minute incubation, 2×SDS-PAGE gel sample dye was added and the sample heated to 95 C for five minutes to denature the proteins. The denatured samples were then subjected to standard SDS-PAGE using a 4 percent stacking gel and 10 percent separating gel. Transfer to PVDF membrane, Western blot with anti-Stat-1 antibody, and color development were performed exactly as described above.

II. Analysis of Results

FIG. 1 represents a densitometric scan of a Western blot detecting Stat-1 protein and Stat-1 protein fragments from PBMC extracts from CFS patients. The value indicated at the top of each lane is the ratio of RNase L fragments as calculated by [(LMW/HMW)*10] as assayed in PBMC extracts from CFS patients. The results demonstrate that the presence and amount of Stat-1 protein fragmentation directly correlates with the presence and amount of low molecular weight RNase L fragments in PBMC samples. These data indicate that native Stat-1 protein is fragmented at an earlier point in the disease cycle than RNase L, and that by the time native RNase L is demonstrably attacked by proteases (ratio>2.0), that native Stat-1 protein has entirely disappeared due to proteolysis, leaving the cells unable to respond to interferons and/or interferon inducers.

Figure 2:
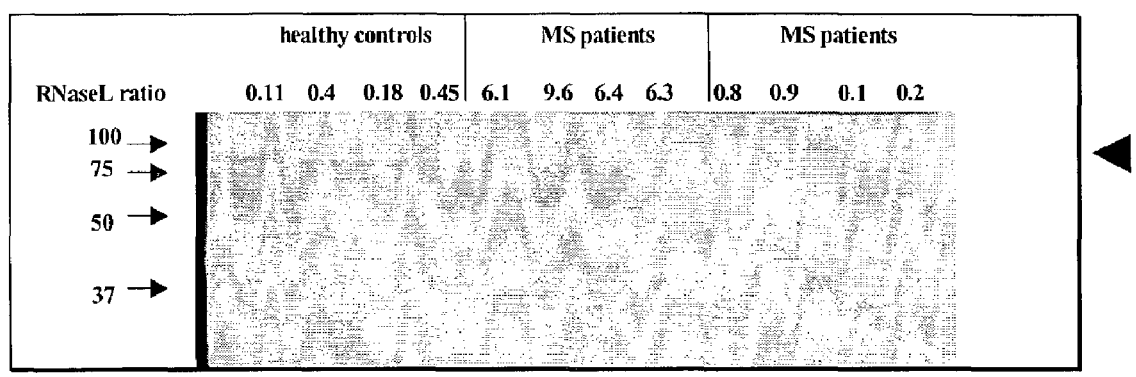
FIG. 2 represents a densitometric scan of a Western blot detecting Stat-1 protein from PBMC extracts of healthy controls and MS patients.

FIG. 2 represents a densitometric scan of a Western blot detecting Stat-1 protein from PBMC extracts from healthy controls and MS patients. The value indicated at the top of each lane is the ratio of RNase L fragments as calculated by [(LMW/HMW)*10] as assayed in PBMC extracts from CFS patients. The results demonstrate that intact, native Stat-1 protein can still be detected in PBMC cell extracts from healthy controls but not in MS patients, even those with low RNase L ratios (e.g., 0.1, 0.2).

Figure 3:
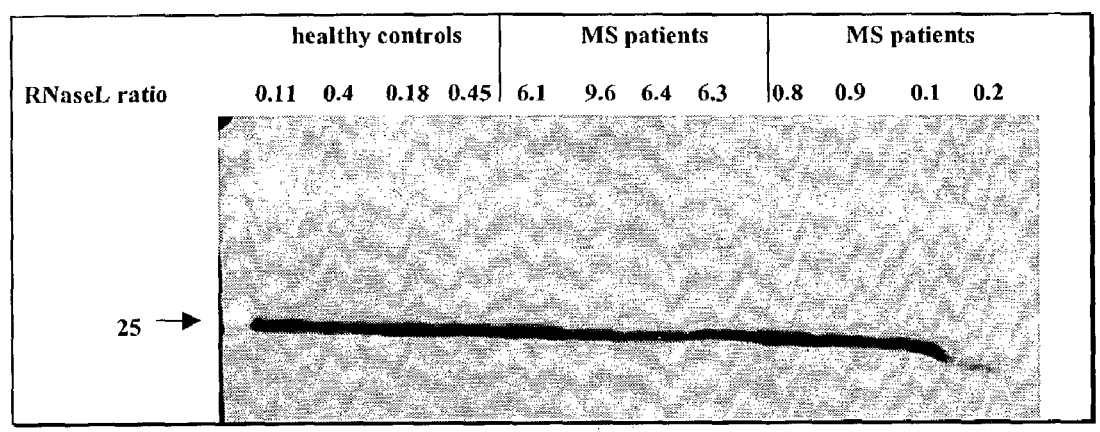
FIG. 3 represents a densitometric scan of a Western blot detecting Bcl-2 as a control for the non-specific degradation of proteins in the PBMC extracts.

FIG. 3 represents a densitometric scan of a Western blot detecting Bcl-2 protein from PBMC extracts from healthy controls and MS patients. As may be observed, in both healthy controls and MS patients, only minor differences may be detected in the level of Bcl-2 protein irrespective of the RNase L ratio, indicating that the disappearance of Stat-1 protein is specific and not an artifact relating to general, non-specific proteolytic degradation.

Figure 4:
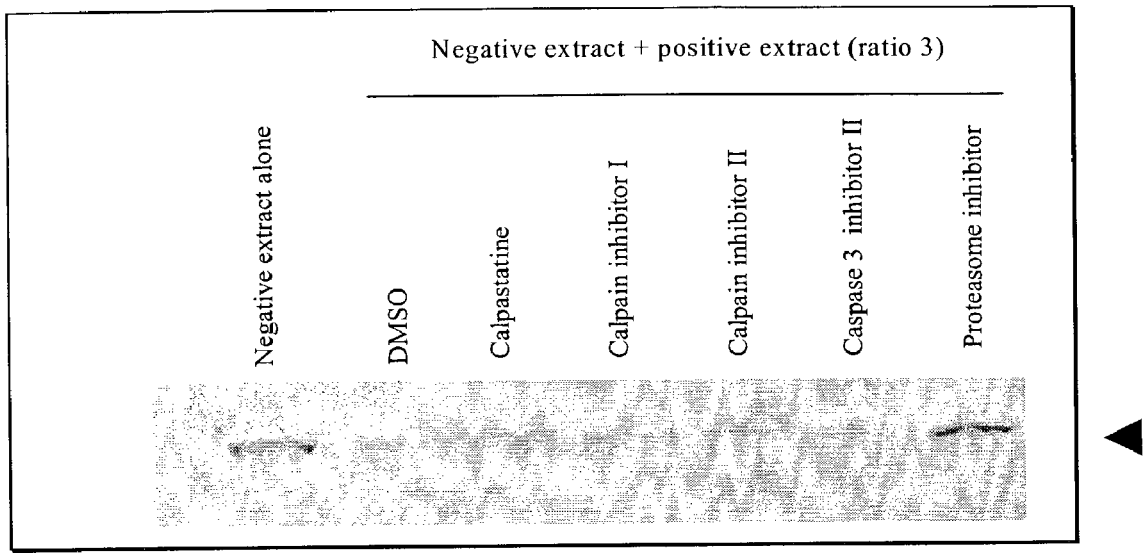
FIG. 4 represents a densitometric scan of a Western blot of PBMC extracts from healthy controls (i.e., RNase L ratio<0.2) mixed with PBMC extracts from CFS patients (i.e., RNase L ratio>2.0) in the absence or presence of protease inhibitors.

FIG. 4 represents a densitometric scan of a Western blot detecting Stat-1 protein from PBMC extracts when mixed in the presence of various protease inhibitors. As may be observed, Stat-1 protein is degraded when a cell extract from a healthy control (i.e., 'negative extract'; RNase L ratio<0.2, Stat-1 protein-containing) is incubated with a cell extract from a patient (RNase L ratio=3.0; Stat-1 protein-negative). This degradation is inhibited in the presence of proteasome inhibitor (MG 132) but not in the presence of the other protease inhibitors tested. Thus the degradation of Stat-1 protein is a specific cellular process that involves the proteasome and does not involve the apoptotic enzymes caspase 3 or calpain.

It is evident from the above results and discussion that relatively simple and rapid methods for diagnosing and/or characterizing chronic immune disease (e.g. MS or CFS) activity in a subject are provided by the subject invention. With the subject methods, accurate diagnosis of the chronic immune disease condition, as well the identification of the stage and/or progression of the chronic immune disease condition, may be obtained. As such, the subject methods provide for more accurate diagnostic and/or treatment regimens. In addition, methods of predicting the effectiveness of particular chronic immune disease treatment protocols, e.g., interferon based treatment regiments, are provided, which results in significant improvements in patient care and resource use. In addition, methods of treating hosts for chronic immune disease are provided. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for diagnosing whether a host suffers from chronic fatigue syndrome (CFS), said method comprising:
   (a) obtaining a peripheral blood mononuclear cell (PBMC) sample from a host;
   (b) assaying said sample from said host obtained in step (a) for the presence of at least one low molecular weight Stat-1 fragment to obtain assay results,
   wherein the presence of a low molecular weight Stat-1 fragment which has a molecular weight that is less than the molecular weight of a full length Stat-1 protein is indicative that said host suffers from CFS;
   (c) diagnosing whether said host suffers from CFS based on whether said at least one low molecular weight Stat-1 fragment is present in said sample.

2. The method according to claim 1, wherein said host is a human.

3. The method according to claim 1, wherein said at least one Stat-1 fragment has a molecular weight from about 15 to about 75 kDa, as measured by SDS-PAGE.

4. The method according to claim 3, wherein said at least one Stat-1 fragment has a molecular weight from about 30 to about 60 kDa, as measured by SDS-PAGE.

5. The method according to claim 4, wherein said at least one Stat-1 fragment has a molecular weight from about 45 to about 50 kDa, as measured by SDS-PAGE.

6. The method according to claim 5, wherein said at least one Stat-1 fragment has a molecular weight of about 50 kDa, as measured by SDS-PAGE.

* * * * *